United States Patent
Chong et al.

(10) Patent No.: US 10,317,351 B2
(45) Date of Patent: Jun. 11, 2019

(54) PRESSURIZED NMR CORE ANALYZER

(71) Applicant: Halliburton Energy Services, Inc., Houston, TX (US)

(72) Inventors: Yuan Chong, Chapel Hill, NC (US); Songhua Chen, Katy, TX (US); Lilong Li, Humble, TX (US); Lizheng Zhang, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/541,013

(22) PCT Filed: Sep. 20, 2016

(86) PCT No.: PCT/US2016/052590
§ 371 (c)(1),
(2) Date: Jun. 29, 2017

(87) PCT Pub. No.: WO2018/056946
PCT Pub. Date: Mar. 29, 2018

(65) Prior Publication Data
US 2018/0259465 A1    Sep. 13, 2018

(51) Int. Cl.
*G01N 24/08* (2006.01)
*G01R 33/30* (2006.01)
(Continued)

(52) U.S. Cl.
CPC .......... *G01N 24/081* (2013.01); *E21B 25/00* (2013.01); *E21B 49/06* (2013.01); *E21B 49/08* (2013.01);
(Continued)

(58) Field of Classification Search
CPC .................................................. G01R 33/305
See application file for complete search history.

(56) References Cited

U.S. PATENT DOCUMENTS 8,362,767 B2    1/2013  Hurlimann et al.
8,791,695 B2    7/2014  Balcom et al.
(Continued)

FOREIGN PATENT DOCUMENTS

WO    WO-2013/171544 A1    11/2013
WO    WO-2015/142531 A1     9/2015
WO    WO-2016/022383 A1     2/2016

OTHER PUBLICATIONS

Chen, et al. "Pore-Connectivity Based Permeability Model for Complex Carbonate Formations," SPWLA 49th Annual Logging Symposium, May 25-28, 2008, held in Edinburgh Scotland, 11 pages.
(Continued)

*Primary Examiner* — Clayton E. LaBalle
*Assistant Examiner* — Jas A Sanghera
(74) *Attorney, Agent, or Firm* — Gilliam IP PLLC

(57) ABSTRACT

Core samples may been collected in a subterranean formation, preserved downhole in a pressurized nuclear magnetic resonance (NMR) core holder (1) comprising components for NMR imaging and (2) capable of maintaining the core samples at downhole fluid saturation state. For example, a pressurized NMR core holder may comprise a housing capable of containing downhole fluid pressures; a coil holder lining an inside of the housing and defining a core chamber; and one or more NMR coils maintained in a longitudinal position along the housing by the coil holder. Further, a system for performing the NMR imaging may comprise: a holder that maintains a pressurized NMR core holder in a desired position; and one or more magnets that are longitudinally movable along the pressurized NMR core holder.

20 Claims, 6 Drawing Sheets

(51) Int. Cl.
    *E21B 49/06*    (2006.01)
    *E21B 25/00*    (2006.01)
    *E21B 49/08*    (2006.01)
    *G01R 33/383*   (2006.01)

(52) U.S. Cl.
    CPC .......... *G01R 33/305* (2013.01); *G01R 33/383* (2013.01)

(56) References Cited

U.S. PATENT DOCUMENTS

| | | |
|---|---|---|
| 2003/0006767 A1 | 1/2003 | Georgi et al. |
| 2003/0155915 A1* | 8/2003 | Kruspe ............ G01R 33/34053 324/303 |
| 2005/0065431 A1* | 3/2005 | Reiderman ............ A61B 5/055 600/415 |
| 2007/0252596 A1* | 11/2007 | Kuge .................. G01N 24/087 324/307 |
| 2009/0128272 A1* | 5/2009 | Hills .................... G01R 33/383 335/306 |
| 2013/0093422 A1* | 4/2013 | Morys ...................... G01V 3/32 324/303 |
| 2013/0261979 A1 | 10/2013 | Al-Muthana et al. |
| 2013/0335081 A1 | 12/2013 | Fordham |
| 2014/0002081 A1 | 1/2014 | Mitchell et al. |
| 2014/0091800 A1 | 4/2014 | Fordham |
| 2014/0225607 A1* | 8/2014 | Edwards ................ G01V 3/32 324/303 |
| 2014/0340082 A1 | 11/2014 | Yang et al. |
| 2015/0061670 A1 | 3/2015 | Fordham et al. |
| 2016/0109603 A1 | 4/2016 | Jin et al. |

OTHER PUBLICATIONS

Chen, et al. "Methods for Computing SWI and BVI from NMR Logs," Western Atlas Logging Services, Houston, Texas, USA and Comodoro, Rivadavia, Argentina, SPWLA 39th Annual Logging Symposium, May 26-29, 1998, 10 pages.

Freedman, et al. "Wettability, Saturation, and Viscosity From NMR Measurements," Society of Petroleum Engineers, Dec. 2003 SPE Journal, 11 pages.

Shafer, et al. "Protocols for Calibrating NMR Log-Derived Permeabilities," Society of Core Analysts, Toronto, Canada, Aug. 21-25, 2005, SCA2005-37, 15 pages.

Sulucarnain, et al., "An NMR Study of Shale Wettability and Effective Surface Relaxivity," Society of Petroleum Engineers, SPE 162236, presented at PE Canadian Unconventional Resources Conference held in Calgary, Alberta, Canada, Oct. 30-Nov. 1, 2012, 11 pages.

Zhang, et al., "Interpretation of Wettability in Sandstones with NMR Analysis," Petrophysics, vol. 41, No. 3, May-Jun. 2000, p. 223-233, Society of Professional Well Log Analysts, originally presented at 1999 International Symposium of the Society of Core Analysts, Aug. 1-4, 1999, Golden, Colorado, paper 9921.

International Search Report and Written Opinion from PCT/US2016/052590, dated Jun. 20, 2017.

* cited by examiner

PRESSURIZED NMR CORE ANALYZER

BACKGROUND

The present application relates to nuclear magnetic resonance (NMR) of core samples.

Often samples of subterranean formations referred to as core samples are acquired via core drilling methods. The core samples are then analyzed to determine the properties (e.g., porosity, oil content, water content, and the like) of the portion of the formation from which they were acquired.

In order to analyze core samples from a subterranean formation, a core apparatus drills a core sample. Once at the surface, the core sample is often preserved by hermetically sealing the core sample in a thick coating of wax or by freezing with dry ice. The purpose of preservation is primarily to maintain the core and any fluids therein and the distribution of those fluids in the core sample as close as possible to reservoir conditions. However, as the native pressure of the core sample is invariably much higher than the pressure at the surface, the gases and light fluids that may have been trapped in the rock will escape from the core sample as it is brought to the surface thus making the core sample less accurate in providing a picture of the subterranean formation from which the core sample was taken.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present application relates to NMR analysis of core samples having been collected in a subterranean formation and preserved downhole in a pressurized core holder, which is referred to herein as a pressurized NMR core holder. Advantageously, the pressurized NMR core holder maintains the core sample at high pressure from downhole collection to NMR measurements at the surface (e.g., at the well site or in an off-site laboratory).

Figure 1A:
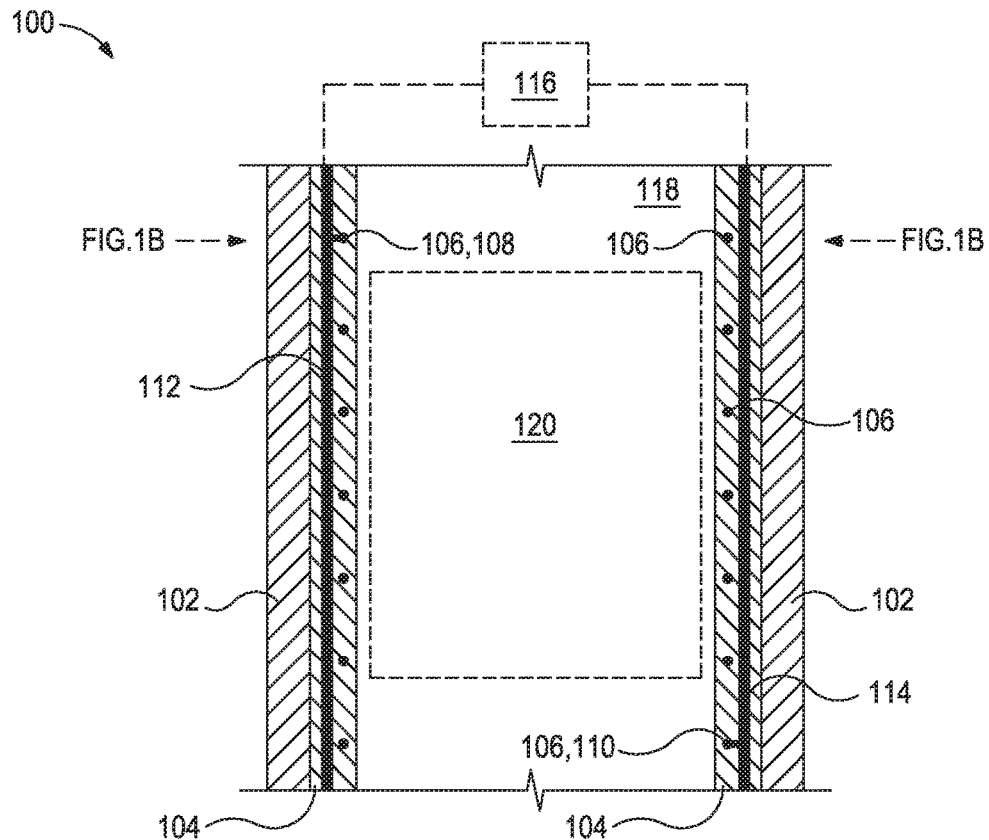
FIGS. 1A and 1B illustrate a cross-sectional side view and cross-sectional top view of a portion of a pressurized NMR core holder.
Figure 1B:
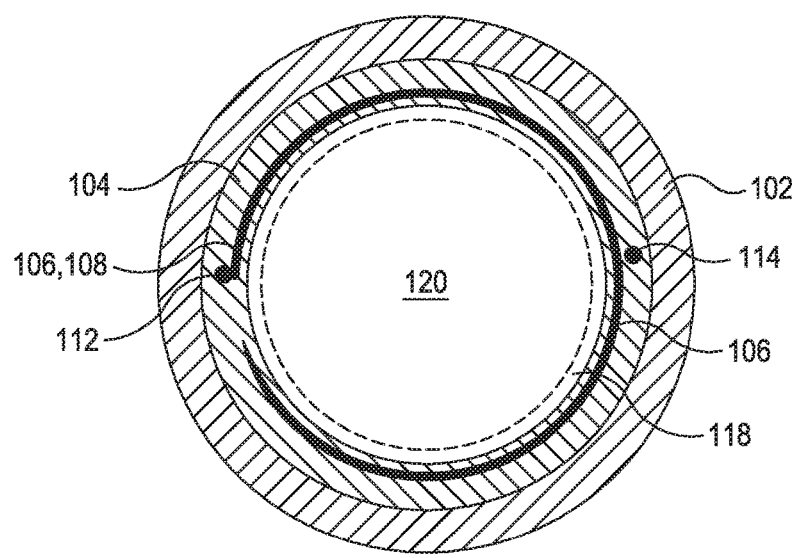

FIGS. 1A and 1B illustrate a cross-sectional side view and cross-sectional top view of a portion of a pressurized NMR core holder 100. The pressurized NMR core holder 100 includes a housing 102 that is capable of containing downhole fluid pressures. A coil holder 104 lines the inside of the housing 102 and maintains one or more NMR coils 106 in position. Each end 108,110 of the NMR coil 106 is connected to a different wire 112,114 that allows for connection to a control system 116.

The control system 116 may be a singular system outside the pressurized NMR core holder 100. For example, the pressurized NMR core holder 100 may include connections that can be used to connect to the control system 116 for NMR measurements. Alternatively, a portion of the control system 116 (e.g., capacitors) may be mounted inside the pressurized NMR core holder 100 and then coupled to the remainder of the control system 116 for NMR measurements.

A core chamber 118 is defined by the coil holder 104 and the housing 102 and is where the core sample 120 is placed. The pressurized NMR core holder 100 may be sufficiently sized to hold between one and twenty core samples 120.

The pressurized NMR core holder 100 may include a cover at one or more ends of the pressurized NMR core holder 100 that can be selectively moved between (1) an open position, where the one or more core samples 120 are able to be inserted into the pressurized NMR core holder 100, and (2) a closed position, where the pressurized NMR core holder 100 is sealed. Accordingly, a cover activation mechanism may be coupled to the pressurized NMR core holder 100 and operable to move the cover between the closed position and the open position.

To maintain the core sample 120 at an elevated temperature, additional thermal components may be added to the pressurized NMR core holder 100 and/or a downhole tool the pressurized NMR core holder 100 is a part of.

Further, the core chamber 118 may be filled with a fluid (also referred to herein as a chamber fluid) (e.g., a non-reactive heavy weight fluid) that is suitable for applying positive pressure to the core samples to mitigate fluids from coming out of the core samples, thereby retaining the core samples native state (or similar thereto) for the later NMR measurements and analysis, as described further herein.

Additionally, in some instances, the fluid may have additional features that support the NMR measurements and analysis. Exemplary fluids may include hydrogen-absent fluids like perfluorocarbons and perchlorocarbons, which allows for 1H NMR measurements to correspond almost exclusively to the core sample and fluids therein. Additionally, fluorinated fluids may be used, which allows for 19F NMR measurements that can be used in conjunction with the 1H NMR measurements to image infiltration of the fluorinated fluids into the core samples, for example.

Generally, the core samples 120 are stored in the pressurized NMR core holder 100 to effectively maintain the reservoir fluids in the core sample in a downhole fluid saturation state. As used herein, the term "downhole fluid saturation state" refers to a state where at least 75% of the fluid in the core sample 120 present when collecting the core sample 120 is maintained in the core sample 120. To achieve a downhole fluid saturation state, the pressurized NMR core holder 100 may maintain a temperature and/or a pressure at or near the downhole collection conditions. In some instances, the fluid pressure in the pressurized NMR core holder 100 may be within about 25% or, more preferably, within about 10% of the fluid pressure the core sample 120 was collected from the formation at. In some instances, the temperature in the pressurized NMR core holder 100 may be within about 25% or, more preferably, within about 10% of the temperature the core sample 120 was collected from the formation at. In some instances, both the temperature and fluid pressure in the pressurized NMR core holder 100 may independently be within about 25% or, more preferably, within about 10% of the temperature and the fluid pressure the core sample 120 was collected from the formation at.

Figure 2:
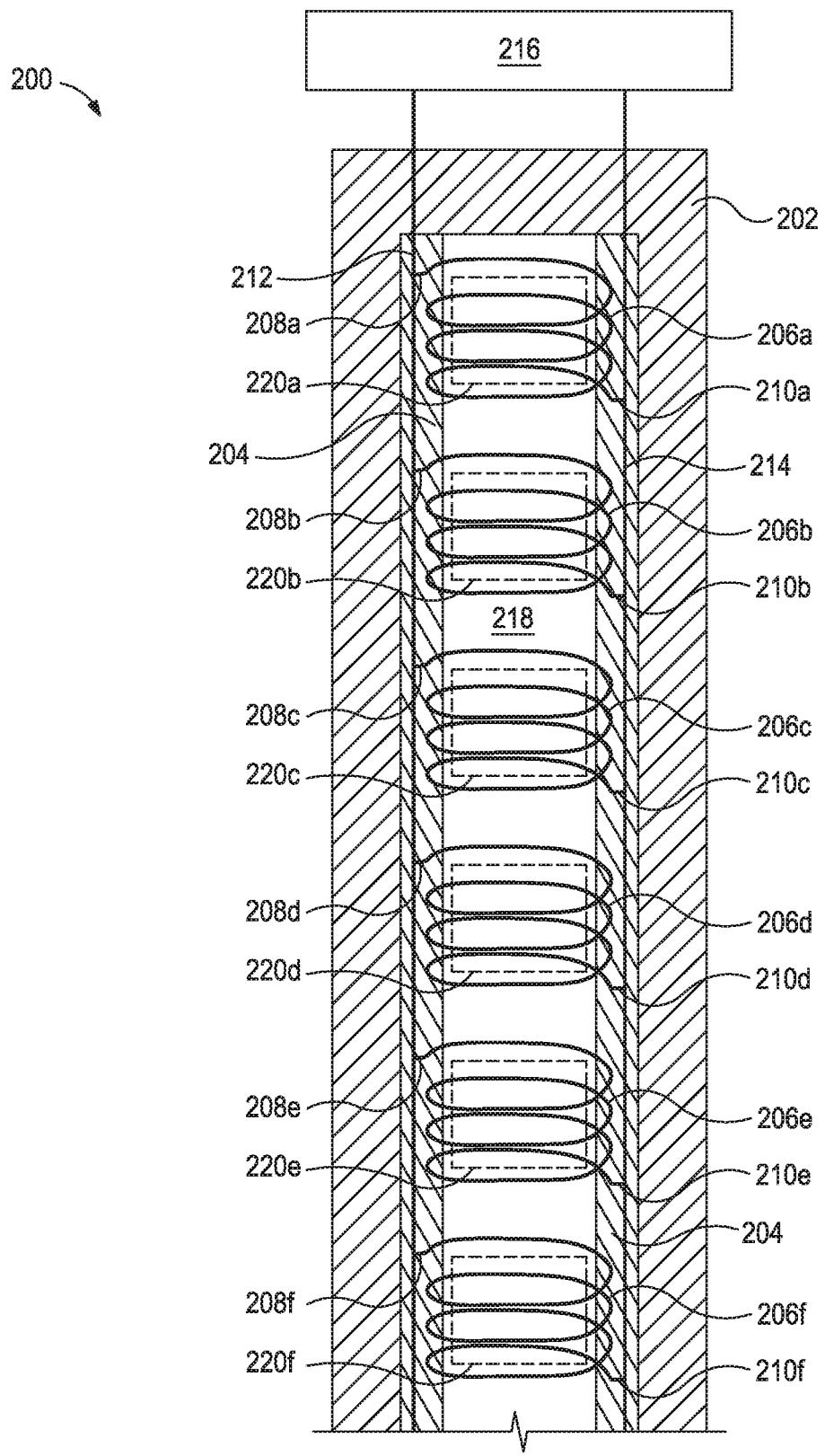
FIG. 2 illustrates a partial cross-sectional side view of a portion of a pressurized NMR core holder.

FIG. 2 illustrates a partial cross-sectional side view of a portion of a pressurized NMR core holder 200. The illustrated portion of the NMR coil holder 200 includes six NMR coils 206a-f in a coil holder 204 and a housing 202. Each end 208a-f,210a-f of the NMR coils 206a-f is connected to wires 212,214, respectively. While FIG. 2 illustrates the wires 212,214 extending through the housing 202, one skilled in the art would recognize that the housing 202 would include ports, seals, and the like to connect wires 212,214 to a control system 216.

When extracted from the subterranean formation by a coring tool (e.g., a sidewall coring tool that extracts core samples from the sidewall of a wellbore or a bottom-hole coring tool that extracts core samples from the bottom of a wellbore), six core samples 220a-f may be placed in the core chamber 218 of the coil holder 204 at locations along the length of the pressurized NMR core holder 200 corresponding to the six NMR coils 206a-f. Then, when retrieved from the wellbore, the pressurized NMR core holder 200 may be connected to the control system 216 (or a portion thereof if some of the control system 216 is part of the pressurized NMR core holder 200) and placed in a magnetic field for taking NMR measurements.

The magnetic field may be generated by a plurality of methods. For example, an electromagnet, a superconducting magnet, a permanent magnet, or a permanent magnet array (e.g., a Halbach array) may be used. The magnets may encompass the pressurized NMR core holder. Alternatively, for permanent magnets, two plate magnets may be placed radially opposing each other relative to the pressurized NMR core holder. Other configuration of magnets can also be implemented to generate a substantially uniform magnetic field inside the core sample volume.

The magnets may be configured to provide a magnetic field along the length of the pressurized NMR core holder. Alternatively, a smaller length magnet (e.g., corresponding to the length of one to a few of the NMR coils) may be used and moved along the pressurized NMR core holder when performing NMR measurements and analysis.

Figure 3:
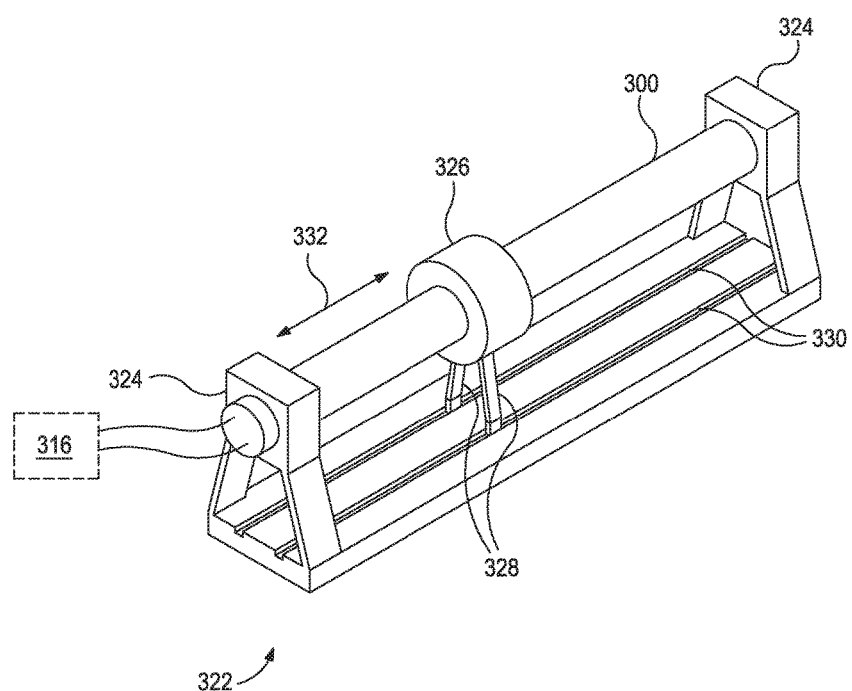
FIG. 3 illustrates an NMR analysis device with a pressurized NMR core holder therein.

For example, FIG. 3 illustrates an NMR analysis device 322 with a pressurized NMR core holder 300 therein. The NMR analysis device 322 includes a holder 324 that maintains the pressurized NMR core holder 300 in a desired position and a magnet 326. The illustrated magnet 326 is on a stand 328 that is longitudinally movable 332 along rails 330 of the NMR analysis device 322. As discussed above, the magnet 326 may be an appropriate length to provide a magnetic field for one to several of the NMR coils in the pressurized NMR core holder 300.

In alternate embodiments, the NMR analysis device may include more than one magnet that is longitudinally movable along the pressurized NMR core holder (e.g., by using two or more stands or by having the two or more magnets on the same stand and longitudinally offset). Further, the NMR analysis device (e.g., NMR analysis device 322 or the foregoing NMR analysis device embodiment with more than one magnet) may be configured such that one or more of the magnets may be removed and replaced with another magnet. For example, the magnet 326 illustrated in FIG. 3 may be a 1.5 Tesla magnet that can be removed from the stand 328 and replaced with a 6 Tesla magnet. The foregoing embodiments may allow for having two or more different magnetic field strengths for performing different NMR measurements (e.g., on different atomic nuclei, different resolution measurements, or different sensitivity measurements). Then, different resonance frequencies may be tuned to with the different magnetic field strengths to obtain NMR measurements corresponding to the different magnetic field strengths.

Figure 4:
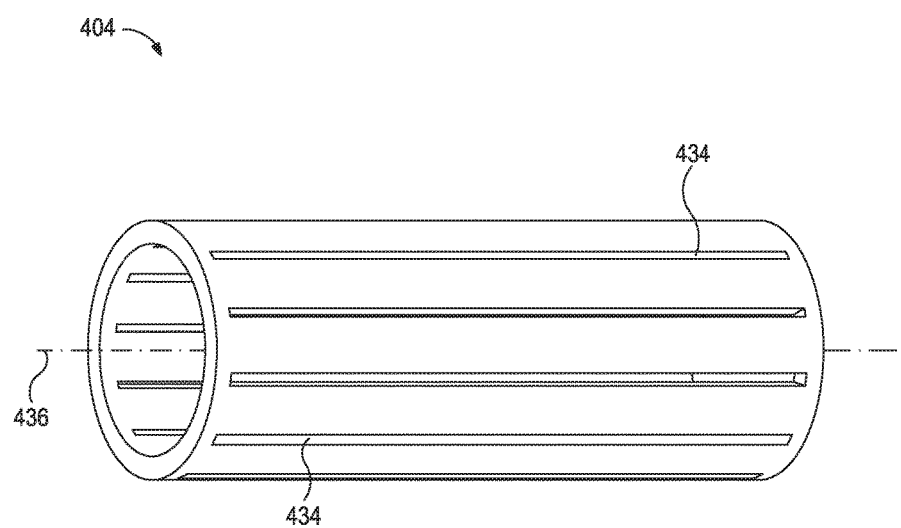
FIG. 4 illustrates a coil holder with a plurality of slits parallel to the longitudinal axis of the coil holder.

The coil holder may have several configurations. For example, in some instances, the coil holder may be a single, solid cylindrical piece that holds more than one NMR coil as illustrated in FIG. 2. Alternatively, the coil holder may be composed of several solid cylindrical pieces with one or more NMR coils in each piece. In some instances, the coil holder may be perforated with holes, slits, or the like. For example, FIG. 4 illustrates a coil holder 404 with a plurality of slits 434 parallel to the longitudinal axis 436 of the coil holder 404.

Perforation in the coil holder may allow for the fluid pressure inside and outside the coil holder to maintain stable, which reduces the overall pressure on the coil holder. By reducing the pressure on the coil holder, the coil holder may be thinner and may not require the coil holder be formed of a strong mechanically material.

Additionally, the perforations may reduce magnetic field shielding and reduce magnetic flux saturation caused by the coil holder.

In some embodiments, the coil holder may be formed of a non-metal material like a polymer or ceramic. Exemplary materials that may be used to form the coil holder may include, but are not limited to, polyether ether ketone (PEEK), polytetrafluoroethylene (PTFE), epoxy, polyimide-based plastics (e.g., VESPEL® polymers available from DuPont), polyxoymethylene (e.g., DELRIN® available from DuPont), a machineable glass-ceramic (e.g., MACOR® ceramics available from Corning, Inc.), zirconia, alumina, titania, and the like, and any combination thereof.

In some embodiments, the coil holder may be formed of a soft magnetic material. As used herein, the term "soft magnetic material" refers to materials that are easily magnetized and demagnetized and typically have an intrinsic coercivity less than 1000 $Am^{-1}$. The use of soft magnetic materials may effectively control the magnetic flux within the coil holder and minimize the Eddy current in a metal housing. While the use of soft magnetic material outside the coil increases the efficiency in delivering the radiofrequency (RF) field and in receiving the NMR signal, it also shields the static magnetic field, which may (1) reduce the static field in the sample region and thereby reduces the NMR frequency and (2) cause field saturation in the soft magnetic material itself. If a higher NMR frequency is desired, one can employ for example a perforated coil holder design (e.g., a slit design illustrated in FIG. 4) to break the transversal circular loop so that static magnetic field in the transversal plane will not be short-circuited. The perforated portions (e.g., the slits) in the coil holder may or may not be filled with another type of material, depending on the mechanical considerations.

Exemplary soft magnetic materials that may be used to form the housing may include, but are not limited to, iron-silicon alloys, nickel-iron alloys, electrically insulated iron particles (e.g., FLUXTROL® materials available from Fluxtrol and MICROMETALS® available from Micrometals), and the like, and any combination thereof.

In some instances, the material that the coil holder is formed of may be protected with a corrosion-resistant, non-metallic composition (e.g., PEEK, PTFE, and the like). As used herein, the term "corrosion-resistant" refers to a composition that has a corrosion rate at least 10% less than the corrosion rate of iron in 1% HCl at 100° C.

For example, the coil holder may be exposed to fluids in the core samples. Therefore, corrosion-resistant, non-metallic composition protection may mitigate corrosion of the coil holder, which may be advantageous when using soft magnetic materials that may include iron. Exemplary protections may include, but are not limited to, a coating, a case, a wrapping, and the like. For example, in some instances, a coil holder may formed at least in part by a soft magnetic material where at least the portion of the coil holder that is the soft magnetic material coated with a corrosion-resistant, non-metallic composition and may optionally be perforated (e.g., with slits). Alternatively, at least the portion of the coil holder that is the soft magnetic material may be wrapped in a tape or ribbon of the corrosion-resistant, non-metallic composition. Alternatively, at least the portion of the coil holder that is the soft magnetic material may be sheathed with a case of the corrosion-resistant, non-metallic composition.

Figure 5:
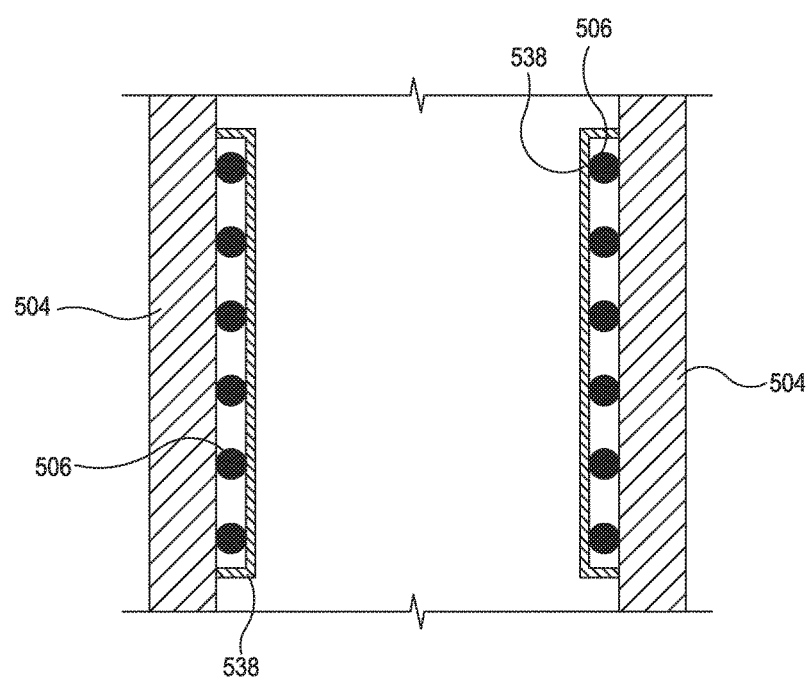
FIG. 5 is a cross-sectional side view of a coil holder with an abutting NMR coil.

The NMR coils relative to the coil holder may have many different configurations. As illustrated in FIGS. 1-2, the NMR coils may be embedded in the coil holder. Alternatively, the NMR coils may abut the coil holder. For example, FIG. 5 is a cross-sectional side view of a coil holder 504 with an abutting NMR coil 506. In some instances, a protective component 538 may optionally be used to hold the NMR coil 506 in place and mitigation damage to the NMR coil 506. The protective component 538 may be sized to contain one or more NMR coils 506. In some instances, not illustrated, the protective component may be a sleeve that extends the length of the coil holder 504. When the coil holder 504 is perforated, the protective component may optionally have corresponding perforations.

The protective component may be formed of a non-metal material like a polymer or ceramic. Exemplary materials that may be used to form the protective sleeve may include, but are not limited to, polyether ether ketone (PEEK), polytetrafluoroethylene (PTFE), epoxy, polyimide-based plastics (e.g., VESPEL® polymers available from DuPont), polyoxymethylene (e.g., DELRIN® available from DuPont), a machineable glass-ceramic (e.g., MACOR® ceramics available from Corning, Inc.), zirconia, alumina, titania, and the like, and any combination thereof.

The housing may be formed of a material capable of withstanding and containing the downhole fluid pressures and temperatures in which the core samples are collected. Exemplary materials that may be used to form the housing may include, but are not limited to, titanium alloys, nickel-cobalt-chromium-molybdenum alloys (e.g., MP35N available from HC Starck), nickel-chromium-based alloys (e.g., INCONEL® alloys available from Special Metals), nickel-based superalloys (HASTELLOY® alloys available from Haynes International, Inc., WASPALOY® alloys available from Haynes International, Inc., and RENE 41® alloys available from Altemp Alloys), stainless steel, and the like, and any combination thereof.

The control system includes the capacitors and switches for taking NMR measurements of the core samples. In some instances, the control system may be configured to perform NMR measurements on different nuclei (e.g., two or more of 1H, 19F, and 23 Na).

The control system also includes a processor for executing the NMR analysis of the core sample. The processor and corresponding computer hardware used to implement the various illustrative blocks, modules, elements, components, methods, and algorithms described herein may be configured to execute one or more sequences of instructions, programming stances, or code stored on a non-transitory, computer-readable medium (e.g., a non-transitory, tangible, computer-readable storage medium containing program instructions that cause a computer system running the program of instructions to perform method steps or cause other components/tools to perform method steps described herein). The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the methods and analyses described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

For example, the processor described herein may be configured for communicating with the NMR coil and related hardware to cause the NMR measurements (e.g., produce RF signals with the RF coil and detect RF signals from the core sample and fluid) and switch between the 1H operational mode and the 19F operational mode as needed. The processor may also be configured to perform the analyses and comparisons described herein. Further, the processor may produce an output that corresponds to the NMR measurements or analyses thereof.

Figure 6:
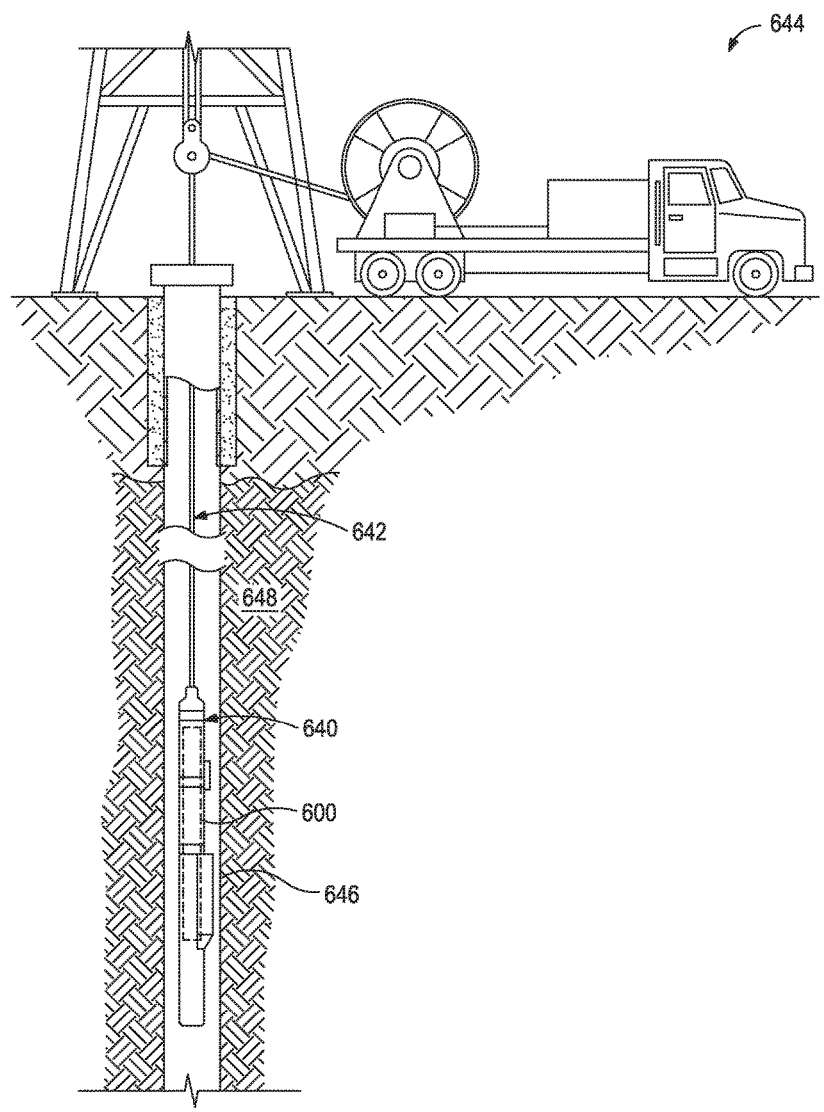
FIG. 6 shows an example system that may employ the principles of the present disclosure.

The pressurized NMR core holder may be used in conjunction with a coring device downhole. For example, FIG. 6 shows an example system 644 that may employ the principles of the present disclosure. In FIG. 6, a coring tool 640 is placed in a wellbore 646 penetrating a subterranean formation 648 by a conveyance, illustrated as a wireline 642 conveyance. The coring tool 640 includes a pressurized NMR core holder 600 described herein. In certain example embodiments, the coring tool 640 is placed in the wellbore 646 by another conveyance (e.g., coil tubing, wired coiled tubing, slickline, and the like) that is connectable to the surface.

Embodiments described herein include, but are not limited to, Embodiment A, Embodiment B, and Embodiment C.

Embodiment A is a pressurized NMR core holder comprising: a housing capable of containing downhole fluid pressures; a coil holder lining an inside of the housing and defining a core chamber; and one or more NMR coils maintained in a longitudinal position along the housing by the coil holder.

Embodiment B is a coring tool comprising the pressurized NMR core holder of Embodiment A.

Optionally, Embodiments A and B may further include one or more of the following: Element 1: wherein the coil holder has perforations therein; Element 2: wherein the coil holder is formed of a material comprising a soft magnetic material and wherein the soft magnetic material is optionally coated with a corrosion-resistant, non-metallic composition; Element 3: the pressurized NMR core holder further comprising: a first wire coupled to a first end of each of the one or more NMR coils and extending along the coil holder; and a second wire coupled to a second end of each of the one or more NMR coils and extending along the coil holder; Element 4: wherein the one or more NMR coils is six or more NMR coils; Element 5: the pressurized NMR core holder further comprising: at least a portion of a control system capable of switching at least one of the one or more NMR coils from a 1H NMR mode to a 19F NMR mode; Element 6: wherein the core chamber contains a hydrogen-absent fluid; and Element 7: wherein the core chamber contains a fluorinated fluid. Exemplary combinations may include, but are not limited to, two or more of Elements 1-3 in combination and optionally in further combination with one or more of Elements 4-7; Element 4 in combination with one or more of Elements 1-3; Element 4 in combination with one or more of Elements 5-7 and optionally further in combination with one or more of Elements 1-3; Element 5 in combination with one or more of Elements 1-4; Element 5 in combination with one or more of Elements 6-7 and optionally further in combination with one or more of Elements 1-4; and the like. Further, the system of Embodiment B may further comprise a wellbore penetrating a subterranean formation and a conveyance coupled to the coring tool, wherein the coring tool is located in the wellbore.

Embodiment C is system comprising: a holder that maintains a pressurized NMR core holder (e.g., according to Embodiment A optionally with one or more of Elements 1-7) in a desired position; and one or more magnets that are longitudinally movable along the pressurized NMR core holder.

Optionally, Embodiments A and B may further include one or more of the following: Element 8: wherein the one or more magnets comprise a first magnet having a first magnetic field strength and a second magnet having a second magnetic field strength different than the first magnetic field strength; Element 9: Element 8 and wherein different resonance frequencies are tuned to with the first and second magnetic field strengths to obtain NMR measurements corresponding to the first and second magnetic field strengths; Element 10: wherein the one or more magnets comprise a Halbach array of magnets; a coil holder lining an inside of the housing and defining a core chamber; and one or more NMR coils maintained in a longitudinal position along the housing by the coil holder; Element 11: the system further comprising: a control system capable of switching at least one of the one or more NMR coils from a 1H NMR mode to a 19F NMR mode; Element 12: wherein at least one of the one or more magnets is removable from the system; and Element: the system further comprising the pressurized NMR core holder secured in the holder, wherein the pressurized NMR core holder is according to Embodiment A optionally with one or more of Elements 1-7. Exemplary combinations may include, but are not limited to, Element 8 and optionally Element 9 in further combination with one or more of Elements 10-12; two or more of Elements 10, 12 and 13; Element 14 in combination with any of the foregoing; Element 14 in combination with one or more of Elements 8-12; and the like.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A pressurized nuclear magnetic resonance (NMR) core holder comprising:
    a housing capable of containing downhole fluid pressures;
    a coil holder lining an inside of the housing and defining a core chamber; and
    one or more NMR coils maintained in a longitudinal position along the housing by the coil holder, wherein the coil holder is composed of soft magnetic material.

2. The pressurized NMR core holder of claim 1, wherein the coil holder has perforations therein.

3. The pressurized NMR core holder of claim 1 further comprising:
    a first wire coupled to a first end of each of the one or more NMR coils and extending along the coil holder; and
    a second wire coupled to a second end of each of the one or more NMR coils and extending along the coil holder.

4. The pressurized NMR core holder of claim 1, wherein the one or more NMR coils is six or more NMR coils.

5. The pressurized NMR core holder of claim 1 further comprising:
    at least a portion of a control system capable of switching at least one of the one or more NMR coils from a 1H NMR mode to a 19F NMR mode.

6. The pressurized NMR core holder of claim 1, wherein the core chamber contains a hydrogen-absent fluid.

7. The pressurized NMR core holder of claim 1, wherein the core chamber contains a fluorinated fluid.

8. The pressurized NMR core holder of claim 1, wherein the soft magnetic material includes iron-silicon alloys, nickel-iron alloys, electrically insulated iron particles, or any combination thereof.

9. A system comprising:
    a holder that maintains a pressurized nuclear magnetic resonance (NMR) core holder in a desired position, wherein the core holder houses a coil holder composed of soft magnetic material; and
    one or more magnets that are longitudinally movable along the pressurized NMR core holder.

10. The system of claim 9, wherein the one or more magnets comprise a first magnet having a first magnetic field strength and a second magnet having a second magnetic field strength different than the first magnetic field strength.

11. The system of claim 10, wherein different resonance frequencies are tuned to with the first and second magnetic field strengths to obtain NMR measurements corresponding to the first and second magnetic field strengths.

12. The system of claim 9, wherein the one or more magnets comprise a Halbach array of magnets.

13. The system of claim 12 further comprising:
    a control system capable of switching at least one or more NMR coils from a 1H NMR mode to a 19F NMR mode.

14. The system of claim 9 further comprising:
    the pressurized NMR core holder secured in the holder and comprising:
        a housing capable of containing downhole fluid pressures;
        a coil holder lining an inside of the housing and defining a core chamber; and
        one or more NMR coils maintained in a longitudinal position along the housing by the coil holder.

15. A system comprising:
    a coring tool comprising a pressurized nuclear magnetic resonance (NMR) core holder that comprises:
        a housing capable of containing downhole fluid pressures;
        a coil holder lining an inside of the housing and defining a core chamber, wherein the coil holder is composed of soft magnetic material; and
        one or more NMR coils maintained in a longitudinal position along the housing by the coil holder.

16. The system claim 15, wherein the coil holder has perforations therein.

17. The system claim 15 further comprising:
    a first wire coupled to a first end of each of the one or more NMR coils and extending along the coil holder; and
    a second wire coupled to a second end of each of the one or more NMR coils and extending along the coil holder.

18. The system claim 15, wherein the one or more NMR coils is six or more NMR coils.

19. The system claim 15 further comprising:
    at least a portion of a control system capable of switching at least one of the one or more NMR coils from a 1H NMR mode to a 19F NMR mode.

20. The system claim 15, wherein the soft magnetic material includes iron-silicon alloys, nickel-iron alloys, electrically insulated iron particles, or any combination thereof.

* * * * *